United States Patent
Lathbury et al.

(12)
(10) Patent No.: US 6,361,497 B1
(45) Date of Patent: *Mar. 26, 2002

(54) CONTROL PANEL FOR INTRAVASCULAR ULTRASONIC IMAGING SYSTEM

(75) Inventors: Georgi Lathbury, Fremont; Niyazi Beyhan, Santa Clara; Thomas C. Moore, Fremont; Sharon Liberty, Santa Clara, all of CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/611,374

(22) Filed: Jul. 7, 2000

Related U.S. Application Data

(63) Continuation of application No. 09/167,055, filed on Oct. 6, 1998, now Pat. No. 6,142,940.

(51) Int. Cl.⁷ .................................................. A61B 8/00
(52) U.S. Cl. ....................................................... 600/437
(58) Field of Search ................................ 600/437, 443, 600/447, 459; D24/158, 100, 186

(56) References Cited

U.S. PATENT DOCUMENTS

| | | | |
|---|---|---|---|
| 5,161,535 A | 11/1992 | Short et al. | 128/660.01 |
| D334,062 S | 3/1993 | Davis et al. | D24/160 |
| D334,981 S | 4/1993 | Davis et al. | D24/160 |
| 5,255,682 A | 10/1993 | Pawluskiewicz et al. | 128/662.03 |
| 5,315,999 A | 5/1994 | Knicki et al. | 128/660.07 |
| 5,379,771 A | 1/1995 | Kawasaki et al. | 128/661.1 |
| D360,690 S | 7/1995 | Murakami | D24/160 |
| D365,148 S | 12/1995 | Murakami et al. | D24/160 |
| D368,521 S | 4/1996 | Asai et al. | D24/160 |
| D379,231 S | 5/1997 | Ungari | D24/160 |
| 5,722,412 A | 3/1998 | Pflugrath et al. | 128/660.07 |
| D398,059 S | 9/1998 | Kwak | D24/160 |
| 5,817,024 A | * 10/1998 | Ogle et al. | 600/447 |
| 5,941,824 A | 8/1999 | Hwang | 600/437 |
| 6,084,576 A | * 7/2000 | Leu et al. | 345/168 |
| 6,142,940 A | * 11/2000 | Lathbury et al. | 600/137 |

FOREIGN PATENT DOCUMENTS

EP 0 501 819 A2 9/1992 ............ A61B/8/12

* cited by examiner

Primary Examiner—Francis J. Jaworski
(74) Attorney, Agent, or Firm—Lyon & Lyon LLP

(57) ABSTRACT

A control panel for an ultrasonic imaging system. A pointing device such as a track ball is centrally located on the control panel and a plurality of buttons and control knobs are arranged around the pointing device in a manner that is ergonomically improved and enhances intuitive system operation. For example, a plurality of image mode selection buttons may be arranged in a substantially linear fashion and located above the pointing device on the control panel. The imaging mode selection buttons preferably are arranged from left to right in order of anticipated use or in order of anticipated frequency of use.

15 Claims, 2 Drawing Sheets

CONTROL PANEL FOR INTRAVASCULAR ULTRASONIC IMAGING SYSTEM

CROSS REFERENCE TO RELATED APPLICATIONS

The present application is a continuation of U.S. application Ser. No. 09/167,055, filed on Oct. 6, 1998 and now U.S. Pat. No. 6,142,940. The priority of the prior application is expressly claimed and its disclosure is hereby incorporated by reference in its entirety.

BACKGROUND OF THE INVENTION

For the past several years, substantial attention has been directed to the field of intravascular ultrasonic imaging systems. Such systems generally include an imaging catheter assembly, a motor drive unit and an imaging subsystem. The imaging catheter assembly is coupled to the motor drive unit, and the motor drive unit is coupled to the imaging subsystem. An imaging transducer is provided within a distal extremity of the catheter assembly and is electronically coupled to the imaging subsystem via the motor drive unit. Conventional imaging subsystems generally include a computer-based image processing system and a display. Thus, when the distal extremity of the catheter assembly is inserted, for example, into a body lumen such as a coronary vessel, an image of an interior surface and/or the structures comprising a wall of the lumen may be depicted on the display. This enables physicians to gain valuable information regarding, for example, occlusions that may exist within, for example, coronary vessels due to the build-up of atherosclerotic plague.

While intravascular ultrasonic imaging systems are very valuable tools to physicians, the use of such systems is often quite complicated and non-intuitive. One reason for this is that the control panels of such systems are not laid out in an intuitive manner. Indeed, conventional control panels are often cluttered with buttons, potentiometers, track balls, and other devices that are not well organized and, as a result, substantial training is often required to educate imaging personnel with regard to even basic imaging functions that are performed by such systems.

Accordingly, it is believed that those skilled in the art would find an innovative control panel with improved ergonomic features and/or an intuitive control group layout to be quite useful.

SUMMARY OF THE INVENTION

In one innovative aspect, the present invention is directed to an innovative control panel for an intravascular ultrasonic imaging system. The control panel preferably has a centrally located track ball, or other pointing device, and a plurality of subsystem control groups that are arranged around the pointing device in an intuitive manner.

For example, in one preferred embodiment, a plurality of imaging mode selection buttons are provided within a region of the control panel just forward of the pointing device and within a region of the control panel that is generally below a display screen of the imaging system. The imaging mode selection buttons preferably are arranged from left to right in order of anticipated use and/or in order of anticipated frequency of use.

Similarly, in another preferred embodiment, an imaging initiation button, record button and pullback button are arranged in a linear fashion adjacent one side of the pointing device. For example, in a presently preferred embodiment, the image initiation, record and pullback buttons are located directly to the left of the pointing device and are arranged in anticipated order of use from a forward region of the control panel to a rearward region of the control panel. It will be appreciated that the term "forward," as used herein, refers to a location generally further away from a user of the system, whereas the term "rearward" is meant to denote a location closer to a user of the system. Thus, when initiating an imaging sequence, a user of a system in accordance with the present invention may reach out to depress the image initiation button and, upon withdrawing his or her hand or arm, easily depress the record button and, if desired, the pullback button.

In still other innovative embodiments, the pointing device is located in a region between an image processing control group and an image analysis control group. The image processing control group may comprise, for example, a depth of field or "zoom" control knob and a plurality of gain control devices including a master gain control knob, a plurality of time gain control potentiometers and a time gain control (TGC) on/off switch. The image analysis control group may comprise, for example, a trace assist button, a bookmark button, a print button and a jog shuttle control assembly including a jog shuttle knob, play button, stop button and pause button.

In a further innovative aspect, the control console may include a pop-out keyboard. Thus, a control panel in accordance with the present invention may take advantage of a relatively large keyboard without limiting to any significant degree the functionality of the control panel.

In view of the foregoing, it is an object of the present invention to provide an improved control panel for use with ultrasonic imaging systems.

It also is an object of the present invention to provide a control panel having improved ergonomic characteristics and an intuitive control group layout such that minimal training is required to operate the controls of the control panel.

Other objects and features of the present invention will become apparent from consideration of the following description taken in conjunction with the accompanying drawings.

DETAILED DESCRIPTION OF PREFERRED EMBODIMENTS

Figure 1:
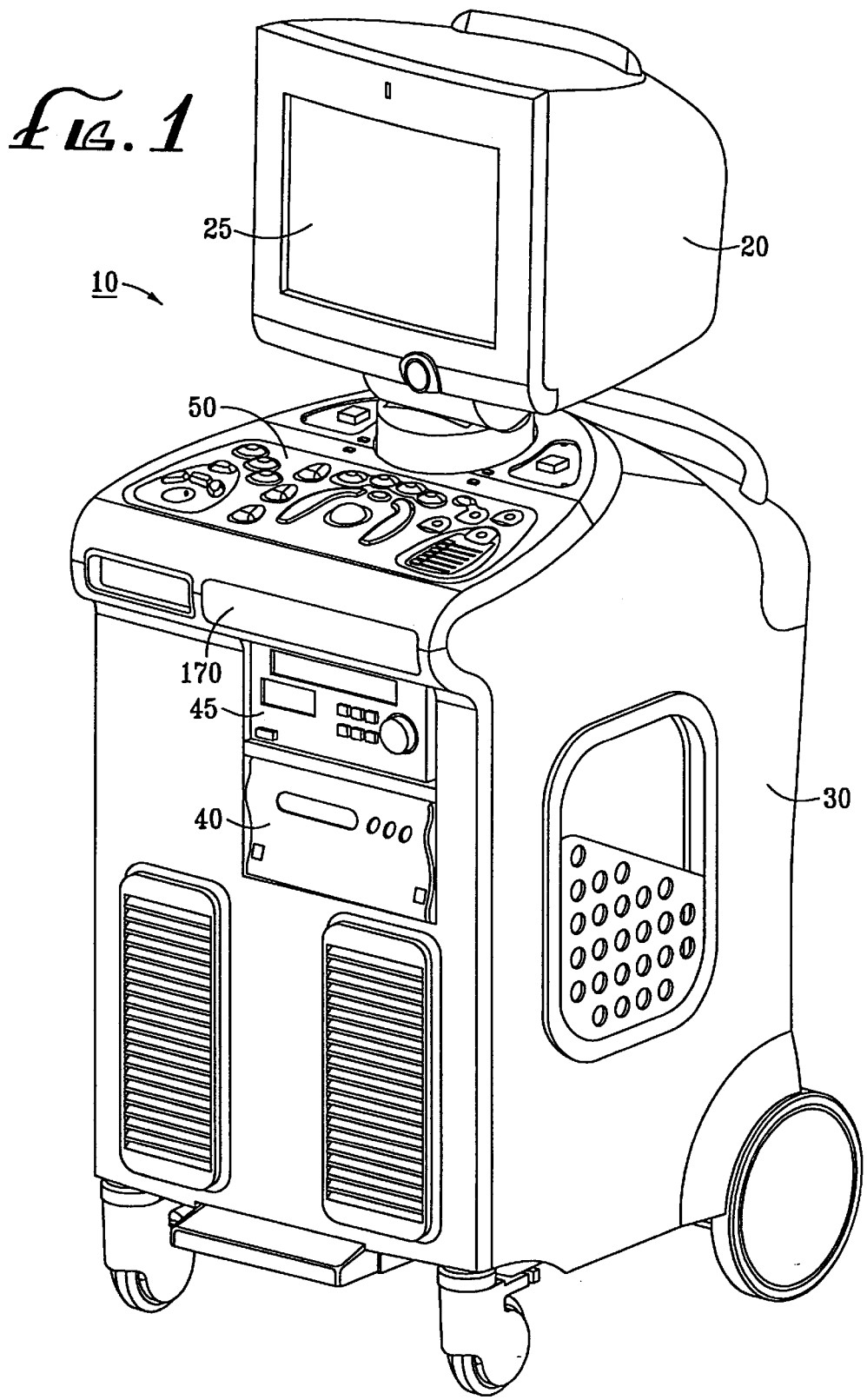
FIG. 1 is an illustration of an intravascular ultrasonic imaging system in accordance with a preferred form of the present invention.

Turning now to the drawings, as shown in FIG. 1, an intravascular ultrasonic imaging system 10 in accordance with the present invention preferably includes a monitor 20 having a display screen 25 for displaying various images (i.e., "tissue ball" ultrasound images, "longview" or vessel cross-sectional images and various X-ray images), and a main chassis assembly 30 for housing a computer-based image processing system (not shown), printer 40 and video recording apparatus 45. As explained above, the image processing unit may be coupled to a motor drive unit (not shown) and the motor drive unit may be coupled to an imaging catheter assembly (not shown) having an imaging transducer (not shown) located within a distal end thereof.

Figure 2:
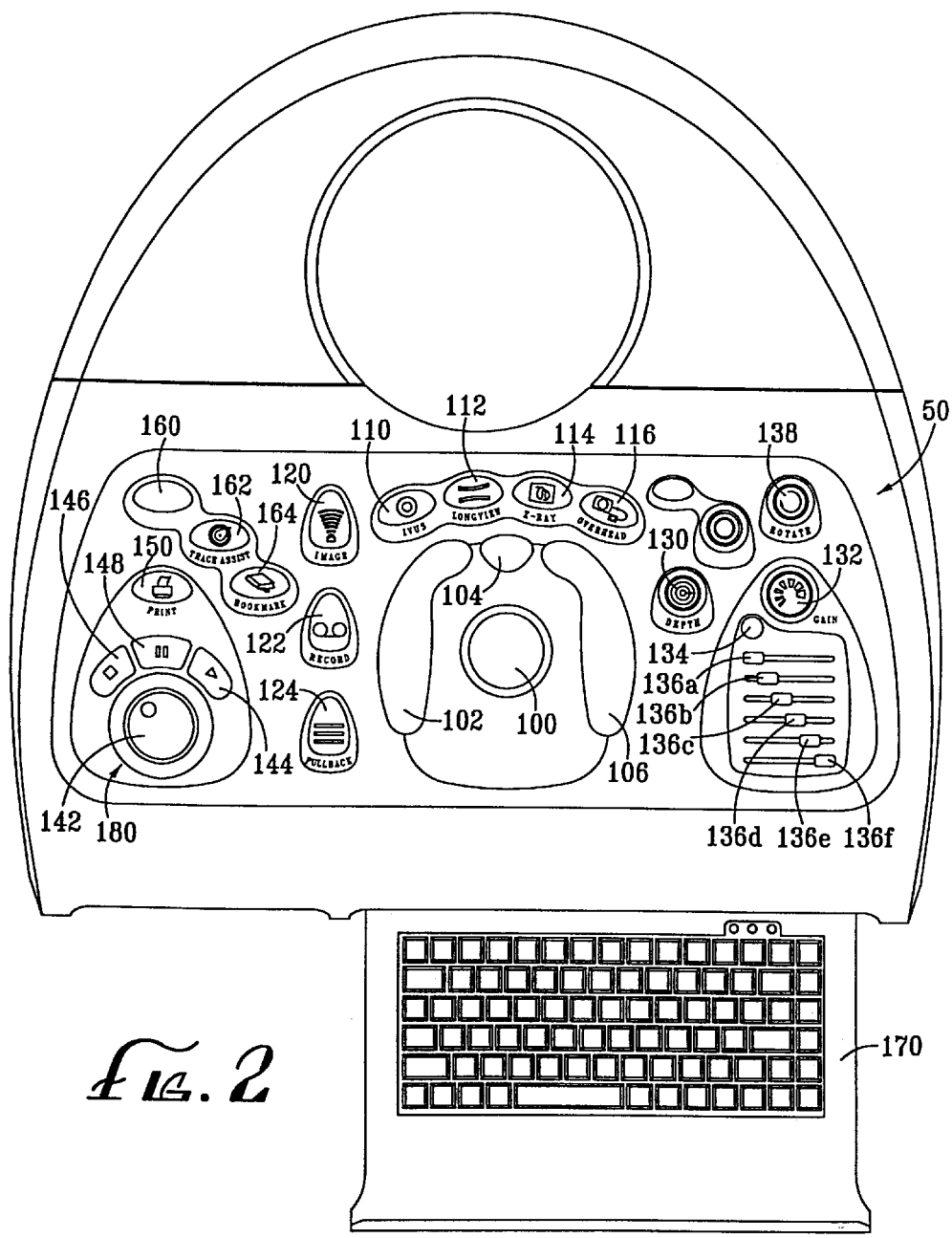
FIG. 2 is a top view of a control panel of the intravascular ultrasonic imaging system shown in FIG. 1.

Turning now to FIG. 2, an innovative control panel 50 is located on an upper surface of the main chassis 30 and directly below the monitor 20. In one particularly preferred embodiment, the control panel 50 includes a centrally located trackball 100 and related "mouse" type control buttons 102, 104 and 106. Those skilled in the art will appreciate that the trackball assembly 100–106 could be replaced by a touch pad mouse (not shown) or by some other pointing device, and that the use of such pointing devices would be equivalent to using the trackball assembly 100–106 illustrated in FIGS. 1 and 2. While the trackball assembly 100–106 need not be located precisely at the center of the control panel 50, it is preferred that the trackball assembly 100–106 be located generally in the center of the control panel 50 to facilitate both right handed and left handed operation of the control panel 50.

A plurality of imaging mode selection buttons 110, 112, 114 and 116 preferably is located within a region of the control panel 50 directly above or forward of the trackball assembly 100. The imaging mode selection buttons preferably include an IVUS image selection button 110, a longview image selection button 112, an x-ray image selection button 114 and an overhead image selection button 116. It will be appreciated that the imaging mode selection buttons 110, 112, 114 and 116 are located on the control panel 50 within a region generally below the display screen 25 of the monitor 20. The image selection control buttons 110, 112, 114 and 116 also preferably are arranged from left to right by order of anticipated use and/or by order of anticipated frequency of use. Finally, the image selection control buttons 110–116 preferably have icons provided on their surfaces for providing an indication of the type of image that will be displayed as the respective buttons 110–116 are depressed. For example, the IVUS image selection button 110 has a "tissue ball" icon provided upon its surface, the longview image selection button 112 has a "vessel cross-section" icon provided upon its surface, and the X-ray image selection button 114 has a heart-vessel image icon provided upon its surface.

The IVUS image selection button 110 preferably functions as an image toggle button that causes an IVUS image or "tissue ball" to be displayed or removed from the main system display 25. This is useful because the system display 25 preferably can depict several images (i.e., tissue ball, longview, x-ray, or saved images). It may be appreciated that in a preferred form the intravascular ultrasonic imaging system 10 shall default to activation of the IVUS image display. That is, following power-up, a full screen IVUS image or tissue ball is displayed on the main system display 25 or monitor 20. During an imaging procedure, a user of the system 10 may add other images to the display 25. When this happens, the system preferably will resize the IVUS image in order to make room on the display 25 for one or more additional images. At this point, pressing the IVUS display button 110 preferably will cause the IVUS image to be removed from the display 25 and will cause any remaining images to be resized to take maximum advantage of available display pixels. Pressing the IVUS display button 110 again preferably redisplays the IVUS image. The IVUS image selection button 110 preferably functions in both live (or active imaging) and digital replay modes.

The longview image selection button 112 functions as a toggle that acts to enable/disable a longview or vessel cross-section display. The default of the system preferably is set to not display a longview image. Thus, pressing the longview image selection button 112 preferably causes any existing image displays to be resized and located in an upper portion of the main display 25 and causes a longview image to be shown horizontally on a lower portion of the display 25.

The x-ray image selection button 114 functions as a toggle that acts to add a x-ray video image onto the system display 20. The x-ray video image may comprise a "roadmap" image or fluoroscopic image. If the IVUS image video is enabled and in the IVUS only mode, then depressing the x-ray button 114 preferably resizes the IVUS display into the upper left corner of the display 25 and places the x-ray image in the upper right corner. Toggling the x-ray image selection button 114 again preferably removes the x-ray video image from the display 25 and resizes the IVUS video image to full screen. It will be appreciated that the x-ray video image may comprise either a "roadmap" or fluoroscopic image, depending upon which type of image is made available from an associated catheter lab x-ray system. However, in some alternative embodiments it may be desirable to allow a user to toggle, for example, between a roadmap and a fluoroscopic image using the x-ray image button 114.

The overhead image selection button 116 enables the imaging system 10 to provide an output of the main display video in a format compatible with that utilized, for example, by x-ray video monitors located within a catheter lab. Thus, through the use of the overhead image selection button 116, it is possible to switch the presentation on the catheter lab x-ray monitor from x-ray images to the main display 25 of the IVUS system 10.

An image on/off button 120, record button 122 and pullback button 124 preferably are arranged in a linear fashion and are located slightly to one side of the track ball assembly 100–106. The image on/off button 120, record button 122 and pullback button 124 preferably are arranged by order of anticipated use with the image on/off button 120 being located within an upper or forward region of the control panel 50, and the pullback button 124 being located within a lower or rearward region of the control panel 50. Thus, those skilled in the art will appreciate that the use of the image on/off button 120, record button 122 and pullback button 124 proceeds in an intuitive manner. First, image depiction is initiated via the image on/off button 120. Then, recording of obtained images is initiated via the record button 122, and a pullback function may be initiated via the pullback button 124.

A plurality of image processing control devices 130–138 preferably are provided within a region of the control panel 50 that is to one side of and adjacent the track ball assembly 100–106. The image processing control devices include a depth control knob 130, gain control knob 132, time gain control on/off switch 134, time gain control potentiometers 136 and image rotation knob 138. The depth control knob 130 enables a user to view more or less of the vessel depth, effectively varying the depth of field of the IVUS image depicted on the display 25. The gain control knob 132 allows a user to raise or lower the overall image gain. This, in effect, acts to raise or lower an entire time gain control curve that may comprise a default setting or a setting defined by the potentiometers 136a–136f. Moreover, the gain control knob 132 allows a user to effect a gain change across an entire time gain control range.

The time gain control on/off switch 134 enables and disables the function of the potentiometers 136a–136f. Thus, the time gain control on/off switch 134 provides a means for preventing alteration of a set time gain control curve and/or alteration of a displayed image in the event that the potentiometers 136 are moved unintentionally.

A video jog shuttle assembly 140 preferably is provided on the control panel 50 within a region opposite the image processing control devices 130–138. The jog shuttle assembly 140 preferably includes a jog shuttle control knob 142, a play button 144, a stop button 146, a pause button 148 and a print button 150. The jog shuttle assembly 140 allows a user to play, fast/slow forward, and fast/slow reverse through recorded images while simultaneously displaying those images. This feature is implemented via a standard VCR-type jog shuttle control for viewing digital cine loop images. It will be appreciated of course that the print button 150 may be used to print any image that is displayed on the monitor 20.

Preferably, a plurality of image analysis buttons 160, 162 and 164 are positioned within a location slightly above the jog shuttle assembly 140 on the control panel 50. The image analysis buttons 160, 162 and 164 preferably include a speckle reduction button 160, trace assist button 162 and bookmark button 164. By depressing the speckle reduction button 160, the user may initiate a speckle reduction subroutine within the image processing system and enable artifact from blood speckle to be removed from a displayed image. Similarly, by depressing the trace assist button 162, the user may initiate a trace assist algorithm that may be used to define an internal and external wall of a vessel displayed on the display 25 of the monitor 20. More specifically, depression of the trace assist button 162 results in enablement of a trace assist function and in the provision of a computer generated graphical representation of a vessel cross-sectional area, the lumen cross-sectional area, the minimum and maximum vessel diameter, and the minimum and maximum lumen diameter. Depressing the trace assist button 162 again preferably disables the trace assist function. Alternatively, depressing the trace assist button 162 could either clear the computer generated graphics, or provide a recalculation if a new set of data has been stored in the display buffer. This latter function would likely occur when the user has forwarded or reversed the digital cine loop paused image.

The bookmark button 164 provides a means for marking a displayed IVUS frame in the digital cine loop to facilitate quick reference to the "marked" frame.

Finally, in one preferred embodiment of the present invention, a pop-out keyboard 170 is provided on the control panel 50. It will be appreciated that when the keyboard is not being used, it may be stored within the control panel 50. Thus, a control panel 50 in accordance with the present invention may take advantage of a relatively large keyboard without limiting to any significant degree the functionality of the control panel 50. Further, by using a pop-out keyboard 170, it is possible to enhance the overall ergonomics of the control panel 50 because the location of the various controls and control groups on the control panel 50 is not dictated by keyboard location.

While the invention is susceptible to various modifications and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A control panel for an ultrasonic imaging system comprising:
   a pointing device located within a central region of the control panel to facilitate both right handed and left handed operation of the pointing device;
   a plurality of imaging mode selection controls located within a region of the control panel forward of the pointing device and generally below a screen of a monitor of the imaging system; and
   the plurality of imaging mode selection controls being arranged by anticipated order of use; and
   wherein the imaging mode selection controls comprise an ultrasound image selection button and an x-ray image button.

2. The control panel of claim 1, further comprising a plurality of image record controls, the image record controls including an image activation button, a record button and a pullback button, the image activation button and the record button and the pullback button being arranged substantially in a line and disposed to one side of the pointing device, and the record button being disposed between the image activation button and the pullback button.

3. The control panel of claim 1, wherein the image activation button is located forward of the record button on the control panel.

4. The control panel of claim 1 further comprising a plurality of image processing controls, the image processing controls being located generally to one side of the pointing device on the control panel, and the image processing controls including a master gain adjustment knob, a plurality of time gain control potentiometers, and a time gain control on/off switch.

5. The control panel of claim 1 further comprising a plurality of image playback controls, the plurality of image playback controls being located generally to one side of the pointing device and including a play button, pause button, stop button and jog shuttle control knob.

6. The control panel of claim 5 further comprising a plurality of image analysis controls located generally forward of the image playback controls on the control panel and comprising a trace assist button and a bookmark button.

7. The control panel of claim 6 wherein the plurality of image analysis controls further comprise a speckle reduction button, the plurality of image analysis controls are arranged in a generally linear fashion, and the trace assist button is located between the speckle reduction and bookmark buttons.

8. The control panel of claim 1, wherein the pointing device comprises a track ball or touch pad.

9. A control panel for an ultrasonic imaging system comprising:
   a pointing device located within a central region of the control panel; and
   a plurality of image record controls including an image activation button, record button and pullback initiation button, the image activation button and the record button and the pullback initiation button being located to one side of the pointing device, the image activation button and the record button and the pullback button being arranged in a line by anticipated order of use with the record button being located generally between the image activation and pullback buttons.

10. The control panel of claim 9 further comprising a pop-out key board.

11. The control panel of claim 9 further comprising a plurality of image processing controls, a plurality of imaging mode selection controls and a plurality of image playback controls, the image processing controls being located to one side of the pointing device, the image playback controls being located to another side of the pointing device, and the imaging mode selection controls being located forward of the pointing device within an area of the control board that is located generally between the image processing controls and the image playback controls.

12. The control panel of claim 11 further comprising a plurality of image analysis controls located generally forward of the image playback controls and located generally between the image playback controls and the imaging mode selection controls.

13. The control panel of claim 12, wherein the image processing controls comprise a master gain control knob, a depth of field control knob, and a plurality of time gain control potentiometers;

the imaging mode selection controls comprise an ultrasonic imaging select button, a longview image select button, an X-ray image select button and an overhead display select button;

the image analysis controls comprise a trace assist button and a bookmark button; and the image playback controls comprises a jog shuttle control knob, a play button, a pause button and a stop button.

14. The control panel of claim 13, wherein the image analysis controls further comprise a speckle reduction button, the image playback controls further comprise a print button, and the image processing controls further comprise an image rotation knob.

15. The control panel of claim 9, wherein the pointing device comprises a track ball or touch pad.

* * * * *